(12) United States Patent
Norimoto

(10) Patent No.: US 10,327,965 B2
(45) Date of Patent: Jun. 25, 2019

(54) ABSORBENT ARTICLE

(71) Applicant: DAIO PAPER CORPORATION, Shikokuchou-shi, Ehime (JP)

(72) Inventor: Yoshimi Norimoto, Sakura (JP)

(73) Assignee: Daio Paper Corporation, Ehime (JP)

( * ) Notice: Subject to any disclaimer, the term of this patent is extended or adjusted under 35 U.S.C. 154(b) by 700 days.

(21) Appl. No.: 14/906,364

(22) PCT Filed: Jul. 25, 2014

(86) PCT No.: PCT/JP2014/069743
§ 371 (c)(1),
(2) Date: Jan. 20, 2016

(87) PCT Pub. No.: WO2015/012399
PCT Pub. Date: Jan. 29, 2015

(65) Prior Publication Data
US 2016/0158074 A1    Jun. 9, 2016

(30) Foreign Application Priority Data

Jul. 26, 2013  (JP) .................................. 2013-155558

(51) Int. Cl.
| | |
|---|---|
| *A61F 13/534* | (2006.01) |
| *A61F 13/512* | (2006.01) |
| *A61F 13/511* | (2006.01) |
| *A61F 13/53* | (2006.01) |
| *A61F 13/84* | (2006.01) |

(52) U.S. Cl.
CPC ........ *A61F 13/534* (2013.01); *A61F 13/5121* (2013.01); *A61F 13/51104* (2013.01); *A61F 2013/530007* (2013.01); *A61F 2013/53445* (2013.01); *A61F 2013/530547* (2013.01); *A61F 2013/530715* (2013.01); *A61F 2013/530737* (2013.01); *A61F 2013/8491* (2013.01)

(58) Field of Classification Search
CPC .......... A61F 2013/53445; A61F 13/512; A61F 13/51104
See application file for complete search history.

(56) References Cited

U.S. PATENT DOCUMENTS

| | | | |
|---|---|---|---|
| 4,251,643 A * | 2/1981 | Harada | ................... A61F 13/53 |
| | | | 525/59 |
| 4,629,643 A | 12/1986 | Curro et al. | |
| | (Continued) | | |

FOREIGN PATENT DOCUMENTS

| | | |
|---|---|---|
| JP | 62-57551 | 3/1987 |
| JP | 8-260329 | 10/1996 |
| | (Continued) | |

*Primary Examiner* — Peter S Vasat
(74) *Attorney, Agent, or Firm* — Norris McLaughlin, P.A.

(57) ABSTRACT

In an absorbent article a three-dimensional opening hole mesh sheet, having a face which faces skin of a wearer of the absorbent article and a reverse or opposite side face within the absorbent article, is combined with an absorber which includes an air-laid pulp non-woven fabric. The mesh sheet has an array of mechanically embossed concave portions forming protrusions on the skin-facing face of the mesh sheet and recesses on the reverse or opposite face, i.e., the unexposed face inside the absorbent article.

4 Claims, 4 Drawing Sheets

(56) References Cited

U.S. PATENT DOCUMENTS

| | | | | |
|---|---|---|---|---|
| 6,710,225 B1* | 3/2004 | Everett | ................ | H01L 27/115 |
| | | | | 257/E21.69 |
| 2003/0135178 A1* | 7/2003 | Hansen | ................ | A61F 13/535 |
| | | | | 604/368 |
| 2014/0188066 A1 | 7/2014 | Mukai et al. | | |
| 2014/0364824 A1 | 12/2014 | Ota et al. | | |

FOREIGN PATENT DOCUMENTS

| | | | |
|---|---|---|---|
| JP | 10-131014 | | 5/1998 |
| JP | 10-508528 | | 8/1998 |
| JP | 10-324750 | | 12/1998 |
| JP | 2012029838 | * | 2/2012 |
| JP | 2013-132434 | | 7/2013 |

* cited by examiner

ABSORBENT ARTICLE

BACKGROUND OF THE INVENTION

The present invention relates to thin absorbent articles, such as a sanitary napkin, a panty liner and an incontinence pad, that use an air-laid pulp non-woven fabric as an absorber.

Conventionally known absorbent articles such as a panty liner, a sanitary napkin or an incontinence pad are those in which an absorber formed of cotton-like pulp or the like is interposed between a liquid-impermeable back surface sheet such as a polyethylene sheet or a polyethylene sheet laminated non-woven fabric and a liquid-permeable front surface sheet such as a non-woven fabric. However, in recent years, a thin absorbent article using, as an absorber, an air-laid pulp non-woven fabric (hereinafter also simply referred to as an air-laid) is known because conventional absorbent articles have poor storability, poor fitting to a body, and because air-laids provide efficiency and resource saving in logistics.

On the other hand, as the liquid-permeable front surface sheet, a small opening polymer web (hereinafter referred to as a three-dimensional opening hole mesh sheet) that has a flexible silk-like texture is disclosed in Japanese Patent No. 2543502. This mesh sheet is a small opening polymer web corresponding to a crater-shaped opening portion that has the following configuration: as shown in FIG. 6, in a small opening polymer web 110 having a flexible silk-like texture on at least one surface, the silk-like texture surface of the web shows, when a distance between the web and the eyes of an observer is at least about 30.5 cm (12 inches), a pattern of discontinuous surface deformation portions 120 formed with openings of apex portions, each of which cannot be identified by normal naked eyes, and each of the surface deformation portions 120 has a substantially vertical height from a surface forming the surface deformation portion 120. At an end portion of each of the surface deformation portions 120, at least one small opening portion 125 is formed so as to substantially match with the maximum height point, and the small opening 125 has a relatively thin and irregularly-shaped petal-shaped portion such that the texture of the web becomes substantially flexible and silk-like and that the compression resistance and the shear resistance of the surface deformation portions 120 and the degree of contact with the skin of the observer are reduced, Japanese Patent No. 2543502 also discloses that macroscopic debossments are formed separately of the small opening 125 (see FIG. 6 of that patent), and that in order for a fluid transport property to an absorber to be enhanced, the bottom surface of these macroscopic debossments is opened as a fluid passage hole (see FIG. 7 of that patent).

Other examples in literature that disclose the three-dimensional opening hole mesh sheet in which, as described above, a large number of small convex portions protruding to the side of the skin are formed and in which the apex portions thereof are opened include Japanese Unexamined Patent Application Publication No. 8-260329 and Japanese Unexamined Patent Application Publication No, 10-131014.

SUMMARY OF THE INVENTION

The following problems are expected with an absorbent article in which the three-dimensional opening hole mesh sheet is combined with an air-laid absorber.

(1) Although it is necessary for the absorber to have a sufficient body fluid absorption capacity so that body fluid is not left on the upper surface of the three-dimensional opening hole mesh sheet, in the case of a thin absorbent article using the air-laid as the absorber, the absorbed amount of body fluid is low compared with a conventional pulp (i.e., not air-laid) absorber. Although in order to compensate for this disadvantage, a method (1) of increasing the weight per unit area; a method (2) of increasing the mixed amount of high-absorbent polymer, i.e., amount of high-absorbent polymer mixed with the air-laid; and the like can be considered, when the weight per unit area is increased, the absorber is thickened and thus the reason for using the air-laid absorber is lost. When the mixed amount of high-absorbent polymer is excessively increased, so-called "gel blocking" occurs in which particles of water-absorbing polymer are so swollen as to provide insufficient gaps therebetween for adequate passage of water or other aqueous liquid such as urine or menstrual fluids, and thus problems occur such as it being impossible to realize desired water-absorbing power, and the high-absorbent polymer migrating in the absorbent article in a manner which results in the absorbent article easily losing shape.

Although patent literature 1 Japanese Patent No. 2543502 (corresponding to U.S. Pat. No. 4,629,643) discloses that macroscopic debossments are formed separately of the small openings, and the bottom surface of each of these macroscopic debossments is open as a fluid passage hole, in order for the absorber to rapidly absorb body fluid such that the body fluid is prevented from being left on the upper surface of the three-dimensional opening hole mesh sheet, the high-absorbent polymer may migrate away from the fluid passage hole in the case of an air-laid absorber in which the mixed amount of high-absorbent polymer is increased.

Hence, a main object of the present invention is that, in an absorbent article in which the three-dimensional opening hole mesh sheet is combined with the air-laid absorber, without the formation of a fluid passage holes having a relatively large opening hole area in addition to small holes in the three-dimensional opening hole mesh sheet, a body fluid on the upper surface of the three-dimensional opening hole mesh sheet can be rapidly absorbed by the absorber, the amount of body fluid absorbed by the absorber can be increased and furthermore, gel blocking caused by a high-absorbent polymer and migration thereof resulting in loss of shape of the absorbent article are prevented.

In order to solve the problem described above, according to a first aspect of the present invention, there is provided an absorbent article in which an absorber is interposed between a liquid-permeable front surface sheet and a back surface sheet, wherein in the liquid-permeable front surface sheet, a large number of small convex portions protruding to a skin side are formed, a three-dimensional opening hole mesh sheet in which the apex of each of the small convex portions has an opening hole is used, and mechanical emboss processing is performed on the three-dimensional opening hole mesh sheet to form a large number of concave portions recessed to a non-skin side, wherein the absorber is an air-laid absorber that has a five-layer structure in which an air-laid pulp non-woven fabric layer, a high-absorbent polymer A layer, an air-laid pulp non-woven fabric layer, a high-absorbent polymer B layer and an air-laid pulp non-woven fabric layer are stacked sequentially from the side of the liquid-permeable front surface sheet, and as a high-absorbent polymer comprising the high-absorbent polymer A layer, a high-absorbent polymer that has physical values of a high water absorption rate relative to a high-absorbent polymer comprising the high-absorbent polymer B layer is used and as the high-absorbent polymer comprising the high-absorbent polymer B layer, a high-absorbent polymer that has physical values of a high absorption capacity relative to the high-absorbent polymer comprising the high-absorbent polymer A layer is used.

In the first aspect of the invention, as the liquid-permeable front surface sheet, a large number of small convex portions protruding to the skin side are formed, the three-dimensional opening hole mesh sheet in which the apex of each of the small convex portions has an opening holes is used, and the mechanical emboss processing is performed on the three-dimensional opening hole mesh sheet to form a large number of concave portions recessed to the non-skin side. Although discharged body fluid passes through the small holes and is thereby transferred to the absorber, since the concave portions temporarily function as a reservoir, the body fluid flows from the small holes rapidly and easily. Since the body fluid relatively rapidly disappears in the convex portions, a wet feel on the skin also rapidly disappears.

Further, since the fluid passage hole which has a relatively large opening hole area is not formed in addition to the small holes in the three-dimensional opening hole mesh sheet, the high-absorbent polymer is prevented from migrating to the outside.

On the other hand, the absorber is the air-laid absorber that has the five-layer structure in which the air-laid pulp non-woven fabric layer, the high-absorbent polymer A layer, the air-laid pulp non-woven fabric layer, the high-absorbent polymer B layer and the air-laid pulp non-woven fabric layer are stacked sequentially on the liquid-permeable front surface sheet, and as the high-absorbent polymer A layer, a high-absorbent polymer that has physical values of a relatively high water absorption rate is used, and as the high-absorbent polymer B layer, a high-absorbent polymer that has physical values of a relatively high absorption capacity is used.

Thus, it is possible to rapidly draw body fluid that has flown in from the front surface sheet into the absorber. Because the thin air-laid absorber is formed with the high-absorbent polymer B layer, a large amount of body fluid can be retained, and thus the absorbed amount of body fluid is increased. Since the high-absorbent polymer is arranged in layers so as to be separated into the A layer and the B layer, the high-absorbent polymer does not migrate, and shapelessness is unlikely to occur.

As a second aspect of the present invention, the absorbent article according to the first aspect of the invention is provided in which, in the high-absorbent polymer comprising the high-absorbent polymer A layer, the water absorption rate in the below water absorption rate test is less than 40 seconds (sec).

Water Absorption Rate Test (1) 50 ml of physiological saline and a stirrer chip are put into a 100 ml beaker, and the beaker is placed on a magnetic stirrer;

(2) the rate of revolution of the magnetic stirrer is set at 600±60 revolution per minute (r.p.m.), an eddy is generated in the physiological saline and thereafter 2.0 g of the polymer is quickly added to the beaker; and (3) a stopwatch is used to measure a time (sec) in which, after the addition of the polymer, the eddy in a surface of liquid in the beaker disappears and the measured time is set as the water absorption rate (see).

As a third aspect of the present invention, the absorbent article according to the first or second aspect of the invention is provided in which, in the high-absorbent polymer comprising the high-absorbent polymer B layer, the absorbed amount in an absorbed amount test below is equal to or more than 70 g (grams):

Absorbed Amount Test (1) 0.5 g of the polymer is put into a tea bag (200 mesh nylon bag), and 100 ml of physiological saline is put into a 200 ml beaker;

(2) the tea bag is immersed for 30 minutes and is hung for 5 minutes after the immersion to remove water, and a mass Wa g is measured;

(3) by performing the same operation, the mass Wb g of the tea an identical bag without the polymer after immersion and hanging is also measured; and (4) the absorbed amount g is determined from Wa g-Wb g/mass g of the polymer.

As a fourth aspect of the present invention, the absorbent article according to any one of the first to third aspects of the invention is provided in which between the liquid-permeable front surface sheet and the absorber, an air-through non-woven fabric (i.e., a non-woven fabric through which air can pass) is interposed.

In the fourth aspect of the invention, between the liquid-permeable front surface sheet and the absorber, the air-through non-woven fabric is interposed, and thus body fluid is easily transferred to the absorber. In other words, since the bulky air-through non-woven fabric is used as the second sheet, and thus there is no gap between the liquid-permeable front surface sheet and the absorber i.e., there is continuity in materials to transport body fluid, body fluid is easily transferred to the absorber.

As a fifth aspect of the present invention, the absorbent article according to any one of the first to fourth aspects of the present invention is provided in which the weight of the absorber per unit area is 150 to 200 g/m$^2$, the combined weight of the high-absorbent polymers with respect to the total weight of the absorber is 30 to 50 weight %, a weight ratio of the high-absorbent polymer comprising the high-absorbent polymer A layer to the high-absorbent polymer comprising the high-absorbent polymer B layer is 1 to 1.5 and an overall thickness is 2 mm or less.

Thus, in a fifth aspect of the present invention, the preferred physical values of the absorber are specifically specified. That is, the weight of the absorber per unit area is preferably set at 150 to 200 g/m$^2$, and the combined weight of the high-absorbent polymer with respect to the total weight of the absorber is preferably set at 30 to 50 weight %. Preferably, a weight ratio of the high-absorbent polymer comprising the high-absorbent polymer A layer to the high-absorbent polymer comprising the high-absorbent polymer B layer is set at 1 to 1.5, i.e., both are set equal in weight or, in order to increase the absorption (i.e., rate of absorption) of body fluid, the high-absorbent polymer comprising the high-absorbent polymer A layer is set at least slightly higher and up to 150 weight % higher than the weight of the polymer B layer. Furthermore, the thickness of the absorber is preferably set at 2 mm or less.

As described above in detail, in the present invention, in the absorbent article in which the three-dimensional opening hole mesh sheet is combined with the air-laid absorber, without the formation of a fluid passage holes each having a relatively large opening hole area in addition to small holes in the three-dimensional opening hole mesh sheet, body fluid on the upper surface of the three-dimensional opening hole mesh sheet can be rapidly absorbed by the absorber, and the amount of body fluid absorbed by the absorber can be increased. Furthermore, gel blocking caused by a high-absorbent polymer, the migration of a high-absorbent polymer, and shapelessness can be prevented.

DETAILED DESCRIPTION OF THE INVENTION

Embodiments of the present invention are described in detail below with reference to drawings.

(Reference Embodiment of Sanitary Napkin 1)

Figure 1:
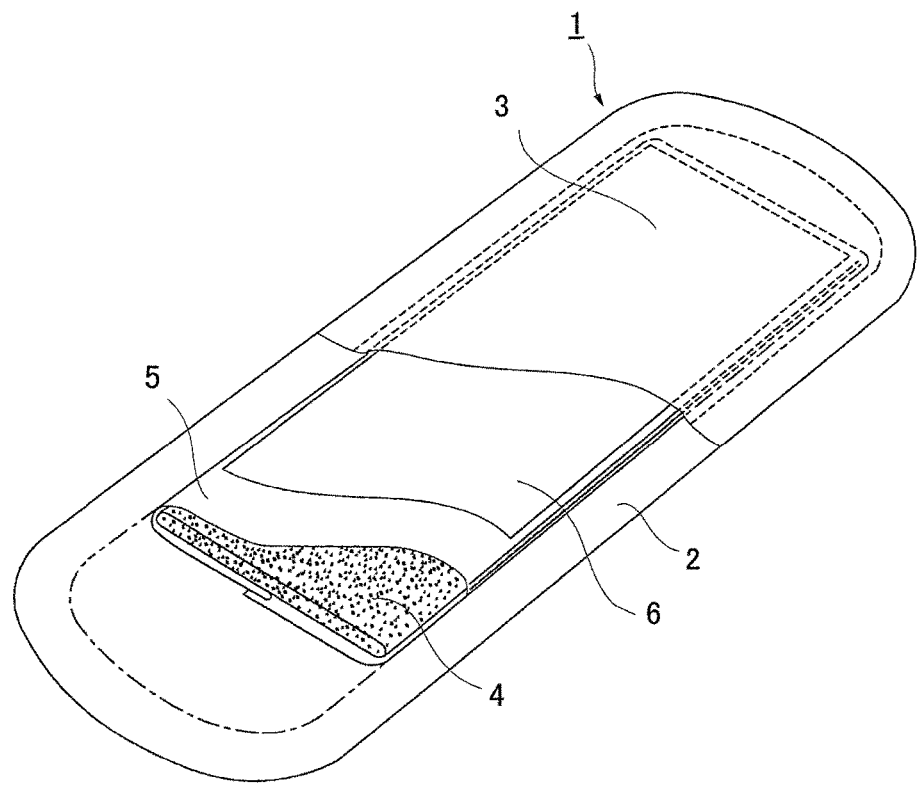
FIG. 1 is a perspective view of an absorbent article (sanitary napkin 1) according to the present invention.

An absorbent article of the invention is generally a panty liner, a sanitary napkin, an incontinence pad and the like, and for example, as shown in FIG. 1, the sanitary napkin 1 is mainly formed with a liquid-impermeable back surface sheet 2 which is formed with a polyethylene sheet or the like, a liquid-permeable front surface sheet 3 which is rapidly permeated by menstrual blood and vaginal discharge and the like, an air-laid absorber 4 which is interposed between both these sheets 2 and 3, crepe paper 5 such as a tissue which surrounds the absorber 4, and a second sheet 6 which is arranged between the liquid-permeable front surface sheet 3 and the absorber 4. Around the absorber 4, the liquid-impermeable back surface sheet 2 and the liquid-permeable front surface sheet 3 are joined with a joining means such as a hot-melt adhesive or the like. The crepe paper 5 may be omitted.

A specific detailed description is given below.

As the liquid-impermeable back surface sheet 2, a sheet material, such as an olefin resin sheet, made of polyethylene or polypropylene, which has at least a water shielding property is used. In addition, a laminate non-woven fabric in which a non-woven fabric is laminated on a polyethylene sheet or the like can be used, and furthermore, as long as liquid impermeability is practically acquired by interposing a waterproof film, a non-woven fabric sheet (in this case, the waterproof film and the non-woven fabric together form the liquid-impermeable back surface sheet) or the like can be used. In recent years, there has been a tendency for a liquid-impermeable back surface sheet which has moisture permeability to be used in order to prevent dampness. This water shielding and moisture permeability sheet material is a microporous sheet obtained by melting and kneading an inorganic filler in an olefin resin such as polyethylene or polypropylene to mold a sheet and thereafter stretching it in a uniaxial or biaxial directions.

Figure 2:
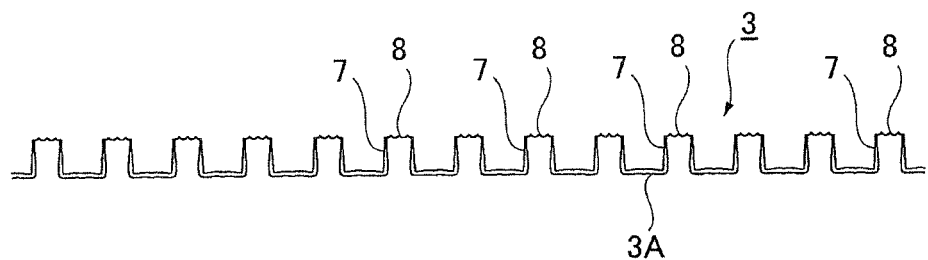
FIG. 2 is a horizontal cross-sectional view of a liquid-permeable front surface sheet 3 before emboss processing.
Figure 3A:
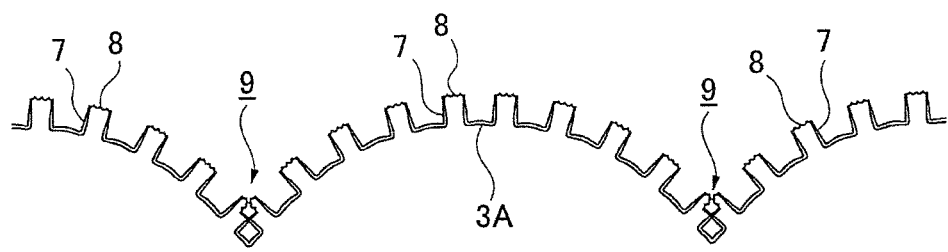
FIGS. 3(A) and 3(B) are horizontal cross-sectional views of the liquid-permeable front surface sheet 3 after the mechanical emboss processing.
Figure 3B:
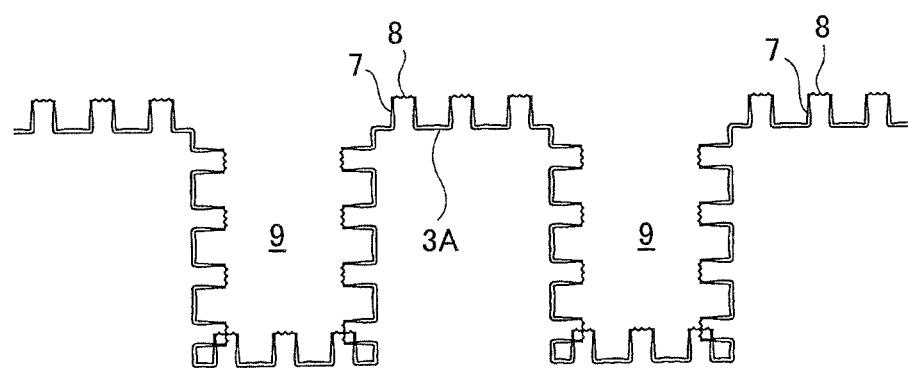

In the liquid-permeable front surface sheet 3, as shown in FIG. 2, a large number of small convex portions 7 protruding to the skin side are formed, a three-dimensional opening hole mesh sheet 3A having a three-dimensional surface structure (three-dimensional small holes) where the apex of each small convex portions 7 has an opening hole 8 is used, and mechanical emboss processing is performed on the three-dimensional opening hole mesh sheet 3A to form a large number of concave portions 9 recessed to the non-skin side as shown in FIG. 3(B).

The diameter of the small convex portion 7 in the three-dimensional opening hole mesh sheet 3A is set at 0.1 to 0.3 mm and is preferably set at 0.13 to 0.27 mm, and the height thereof is set at 0.05 to 0.4 mm and is preferably set at 0.15 to 0.3 mm. The interval between the small convex portions 7 is set at 0.3 to 0.7 mm.

It is substantially impossible to visually recognize whether or not the opening holes 8 of the three-dimensional opening hole mesh sheet 3A are the small convex portions 7, when a distance between the mesh sheet and the eyes of an observer is at least 10 cm. The three-dimensional opening hole mesh sheet 3A as shown in FIG. 2 itself is prior art. As a method of forming the opening holes, a method such as hydro forming (high-pressure liquid jet), vacuum molding, or a needle punch can be used to form the opening holes. Among these opening hole formation methods, since the circumferential edge of the small hole is formed so as to be fluffed (in the shape of a petal), hydroforming (high-pressure liquid jet) and vacuum molding are preferably adopted.

The hydroforming described above is a method in which, when a film is supported on a fine mesh woven wire support member or a support member where a large number of small holes are formed, a high-pressure liquid jet is made to collide with the exposed surface of the web of a flat polymer film, and thus three-dimensional small holes are formed. The vacuum molding described above is a method in which, while a film is present on a fine mesh woven wire support member or a support member where a large number of small holes are formed, a vacuum pressure is made to act by suction from the opposite side to suck the film into the small holes and to swell the film within the small holes and finally the film is ruptured at the tip end to form three-dimensional small holes. As the material of the film, for example, the film of an olefin resin such as polyethylene or polypropylene, or a polyester resin is preferably used. The weight of the film per unit area is preferably set at 20 to 30 g/m$^2$.

In the three-dimensional opening hole mesh sheet 3A, as shown in FIGS. 3(A) and 3(B), the mechanical emboss processing is performed to form a large number of concave portions 9 recessed to the non-skin side. In the mechanical emboss processing, the three-dimensional opening hole mesh sheet 3A is passed between an emboss roll on which a large number of convex portions are formed and an anvil rod on which concave portions corresponding to the convex portions are formed, and thus a large number of concave portions 9 recessed to the non-skin side are formed. The arrangement of the concave portions 9 may be a lattice-shaped arrangement or a staggered arrangement. The concave portions 9 are desirably arranged such that the distance between the centers of the concave portions 9 is 2.0 to 5.0 mm and is preferably 3.0 to 4.0 mm. The shape of the concave portion may be set such that, as shown in FIG. 3(A), a horizontal cross-sectional shape between the embosses is arc-shaped, the concave portions are formed into an inverted cone shape at a boundary portion thereof, or such that, as shown in FIG. 3(B), concave portions 9 recessed in the shape of a circle or an ellipse are formed.

Figure 4:
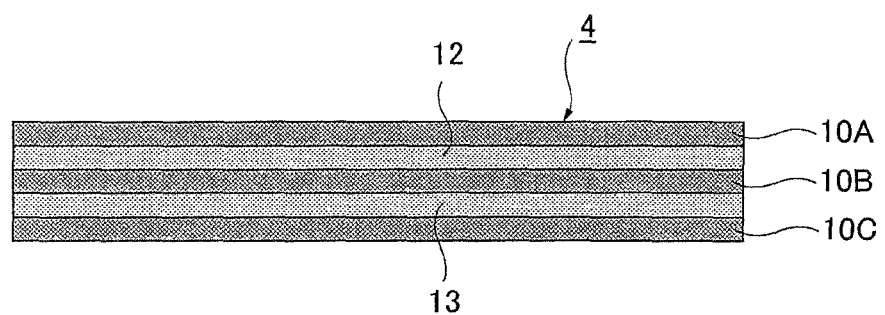
FIG. 4 is a horizontal cross-sectional view showing the configuration of an absorber 4.

The air-laid absorber 4 is described next. As shown in FIG. 4, the air-laid absorber 4 of the present invention has a live-layer structure in which an air-laid pulp non-woven fabric layer 10A, a high-absorbent polymer A layer 12, an air-laid pulp non-woven fabric layer 10B, a high-absorbent polymer B layer 13 and an air-laid pulp non-woven fabric layer 10C are stacked sequentially on the liquid-permeable front surface sheet 3.

The air-laid pulp non-woven fabrics 10A to 10C are a sheet-shaped absorber that is formed as follows: a web is formed by an air-laid method in which fibers having a predetermined length are defibrated, transported along the flow of air, passed through a screen having metal meshes or pores and are thereafter dropped and deposited on a wire mesh, and the intersections of the fibers in the web are thermally fused by a binder fiber or are coupled with an emulsion binder. As the fiber of the air-laid pulp non-woven fabric, a pulp fiber or a thermoplastic short fiber is used. Examples of the thermoplastic fiber include various types of synthetic fibers such as olefins including polypropylene, low-density polyethylene, low-density polyethylene, linear low-density polyethylene and a crystalline propylene copolymer of propylene and α-olefin; polyimides; polyethylene terephthalate; polybutylene terephthalate; a low-melting point polyester copolymerized by diol and terephthalic acid/isophthalic acid; and polyesters such a polyester elastomer.

As the binder fiber described above, a heat-fusible composite fiber is preferably used which is formed of a low-melting point resin and a high-melting point resin that have different melting points and in which the low-melting point resin forms at least part of the fiber surface. As the form of the heat-fusible composite fiber, any composite fiber can be used such as a sheath-core fiber in which a high-melting point fiber is used as a core and in which a low-melting point fiber is used as a sheath, a side-by-side type fiber or a division type fiber.

Although as the emulsion binder, any of a water-based emulsion binder and an organic solvent-based emulsion binder can be used, in terms of handling, safety and the like, a water-based emulsion binder is preferably used. As a binder component, an acrylic resin, a vinyl acetate resin, a styrene-butadiene resin or the like can be used.

Preferably, the weight of the air-laid absorber 4 per unit area is 150 to 200 g/m$^2$, the combined weight of the high-absorbent polymer with respect to the total weight of the air-laid absorber 4 is 30 to 50 weight % and the overall thickness is 2 mm or less. Preferably, a weight ratio of the high-absorbent polymer comprising the high-absorbent polymer A layer 12 to the high-absorbent polymer comprising the high-absorbent polymer B layer 13 is set at 1 to 1.5, i.e., both of them are set equal in weight or in order to increase the absorption (i.e., rate of absorption) of a body fluid, the high-absorbent polymer comprising the high-absorbent polymer A layer 12 is set at least slightly higher and up to 150 weight % higher than the weight of the polymer B layer.

A method of measuring the weight of the air-laid absorber 4 per unit area is to cut out, with a roll cutter, a portion of a sample having a dimension of 20 mm×40 mm (±2 mm), to measure the weight thereof, to convert it into a weight per 1 m$^2$ and to use it as the weight per unit area. With respect to the second sheet 6, which will be described later, by the same method, it is possible to measure the weight per unit area. A method of measuring the thickness of the air-laid absorber 4 is to use a thickness measuring device (peacock, dial thickness gauge large type, model J-B (measurement range of 0 to 35 mm)) made by Ozaki Manufacturing Co., Ltd and to measure the thickness with a sample and the thickness measuring device placed horizontally.

Examples of the high-absorbent polymer used in the high-absorbent polymer A layer 12 and the high-absorbent polymer B layer 13 include a polyacrylate cross-linked product, a self-crosslinked polyacrylic acid salt, an acrylic acid ester-vinyl acetate copolymer cross-linked saponified product, an isobutylene-maleic anhydride copolymer cross-linked product, a polysulfone salt cross-linked product and a product obtained by partially cross-linking a water-swellable polymer such as polyethylene oxide or polyacrylamide. Among them, an acrylic acid or an acrylic acid salt, which is excellent in absorbed amount and water absorption rate, is preferable, in a high-absorbent resin having the water absorption performance described above, in a manufacturing process, the cross-linking density and the cross-linking density gradient are adjusted, thereby making it possible to adjust the absorption power and the water absorption rate.

In the air-laid absorber 4, as the high-absorbent polymer comprising the high-absorbent polymer A layer 12, a high-absorbent polymer that has physical values of a high water absorption rate relative to the high-absorbent polymer comprising the high-absorbent polymer B layer 13 is used, and as the high-absorbent polymer comprising the high-absorbent polymer B layer 13, a high-absorbent polymer that has physical values of a high absorption capacity relative to the high-absorbent polymer comprising the high-absorbent polymer A layer 12 is used.

Specifically, as the high-absorbent polymer comprising the high-absorbent polymer A layer 12, a high-absorbent polymer in which a water absorption rate in the above described water absorption rate test is less than 40 (sec), is preferably 1 to 30 (sec) and is more preferably 25 to 30 (sec) is used.

On the other hand, as the high-absorbent polymer comprising the high-absorbent polymer B layer 13, a high-absorbent polymer in which the absorbed amount in the above described absorbed amount test below is equal to or more than 70 g, is preferably 70 to 80 g and is more preferably 70 to 75 g is used.

The physiological saline used in both the tests described above is physiological saline that contains 0.9 w/v % of sodium chloride ("physiological saline solution" in Japanese pharmacopoeia-prescription drugs).

Between the liquid-permeable front surface sheet 3 and the absorber 4, as the second sheet 6, a hydrophilic non-woven fabric 6 is interposed. Any second sheet 6 can be used as long as it is hydrophilic for body fluid. Specifically, a material which itself is hydrophilic, for example a regenerated fiber such as rayon or cupra or a natural fiber such as cotton, or a non-woven fabric of hydrophobic synthetic fibers which became hydrophilic by treatment with a hydrophilizing agent, the synthetic fibers being of an olefin such as polyethylene or polypropylene, a polyester, a polyamide or the like can be used; a non-woven fabric obtained by an appropriate processing method such as a span lace method, a spun bond method, a thermal bond method, a melt-blown method, a needle punch method or an air-through method can be used. Among these materials, in particular, an air-through non-woven fabric is preferably used. By using an air-through non-woven fabric, which is relatively soft and bulky, a cushioning property is given to achieve a satisfactory fitting feel. Further, since there is no gap between the liquid-permeable front surface sheet 4 and the air-laid absorber 4 so that there is continuity, body fluid is easily transferred to the absorber. The weight of the second sheet 6 per unit area is preferably 15 to 30 g/m$^2$.

Figure 5:
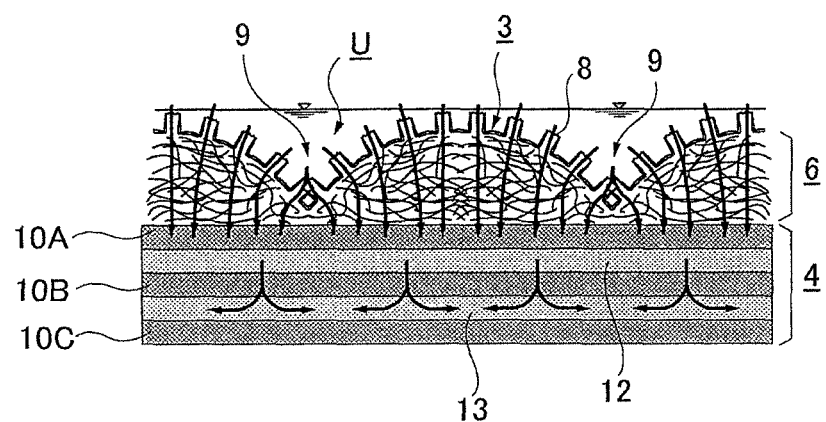
FIG. 5 is a main portion horizontal cross-sectional view for illustrating the absorbed state of a body fluid U.
Figure 6:
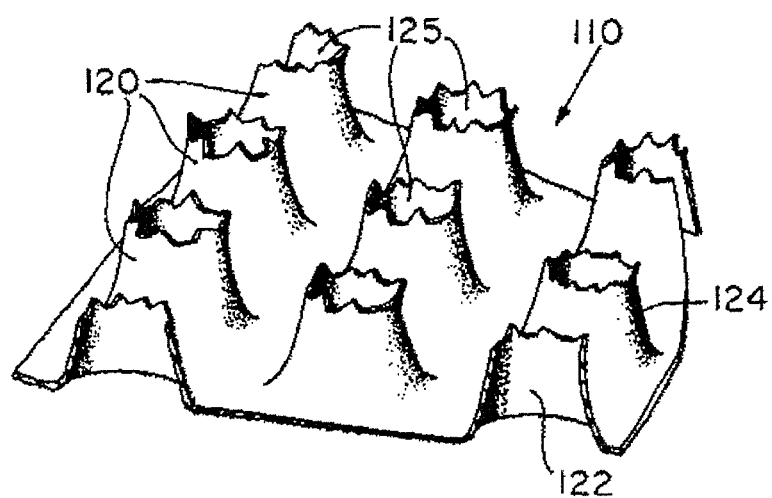
FIG. 6 is a main portion perspective view of a three-dimensional opening hole mesh sheet 110 according to a conventional example.

In the sanitary napkin 1 configured as described above, as shown in FIG. 5, a body fluid U discharged to the upper surface of the liquid-permeable front surface sheet 3 passes through the small holes 8 and is transferred to the absorber 4, and, since the concave portions 9 temporarily function as a tank, the body fluid U flows from the small holes 8 rapidly and easily. Since the body fluid U disappears relatively rapidly in the convex portions, a wet feel on the skin also rapidly disappears.

Since fluid passage holes which have a relatively large opening hole area are not formed in addition to the small holes 8 in the three-dimensional opening hole mesh sheet 3A, the high-absorbent polymer does not migrate outward.

As the high-absorbent polymer A layer 12, a high-absorbent polymer that has physical values of a relatively high water absorption rate is used, and as the high-absorbent polymer B layer 13, a high-absorbent polymer that has physical values of a relatively high absorption capacity is used. Thus, the body fluid U flowing in from the front surface sheet 3 is rapidly drawn into the absorber. Further, because the thin air-laid absorber is formed with the high-absorbent polymer B layer 13, a large amount of body fluid U can be retained, and thus the absorbed amount is increased. Since the high-absorbent polymer is arranged in layers so as to be separated into the A layer 12 and the B layer 13, the high-absorbent polymer does not migrate, and shapelessness is unlikely to occur.

OTHER EMBODIMENTS

Although in the embodiment described above, the high-absorbent polymer A layer 12 is uniformly formed, areas where the high-absorbent polymer is not present may be distributed so that gel blocking is prevented.

The invention claimed is:

1. An absorbent article, comprising an absorber interposed between a liquid-permeable front surface sheet and a back surface sheet, the absorbent article being adapted to be worn by a person with an exposed face of the front surface sheet facing the skin of the person, wherein in the liquid-permeable front surface sheet, a large number of small convex portions protruding to a skin side are formed, the front surface sheet being a three-dimensional opening hole mesh sheet in which the opening holes of the mesh sheet consist of opening holes at apexes of the small convex portions and the mesh sheet has an array of mechanically embossed concave portions forming protrusions on the skin-facing face of the front surface sheet and recesses on a face of the front surface sheet within the absorbent article, the absorber comprises a five-layer structure wherein the layers are, in the following order, sequentially from the front surface sheet, an air-laid pulp non-woven fabric layer, a high-absorbent polymer A layer, a second air-laid pulp non-woven fabric layer, a high-absorbent polymer B layer and a third air-laid pulp non-woven fabric layer, polymer A has a higher water absorption rate than polymer B, polymer B has a higher water absorption capacity than polymer A, and a weight of the absorber per unit area is 150 to 200 g/m², a combined weight of the polymers A and B with respect to a total weight of the absorber is 30 to 50 weight %, a weight ratio of the polymer A to the polymer B is 1 to 1.5 and overall thickness of the absorbent article is not greater than 2 mm.

2. The absorbent article according to claim 1, wherein a water absorption rate of polymer A as measured by a Water Absorption Rate Test is less than 40 (sec).

3. The absorbent article according to claim 2, wherein an absorbed amount of polymer B as measured by an Absorbed Amount Test is at least 70 g.

4. The absorbent article according to claim 3, wherein between the liquid-permeable front surface sheet and the absorber, an air-through non-woven fabric is interposed.

\* \* \* \* \*